(12) United States Patent
Bornstein et al.

(10) Patent No.: US 8,596,286 B2
(45) Date of Patent: Dec. 3, 2013

(54) FLOSSING DEVICE

(75) Inventors: Keith Allen Bornstein, Santa Monica, CA (US); Dan Voetmann, Mountlake Terrace, WA (US)

(73) Assignee: Oralwise, Inc, Dallas, TX (US)

( * ) Notice: Subject to any disclaimer, the term of this patent is extended or adjusted under 35 U.S.C. 154(b) by 0 days.

(21) Appl. No.: 13/169,962

(22) Filed: Jun. 27, 2011

(65) Prior Publication Data

US 2012/0325263 A1    Dec. 27, 2012

(51) Int. Cl.
     *A61C 15/00*      (2006.01)

(52) U.S. Cl.
     USPC ........................................................ 132/323

(58) Field of Classification Search
     USPC .......... 132/309, 321–329, 200; 433/146, 147, 433/216, 141, 134; 84/422.4; D28/65, 66, D28/68; 206/63.3, 63.5
     See application file for complete search history.

(56) References Cited

U.S. PATENT DOCUMENTS

| | | | | |
|---|---|---|---|---|
| 2,180,522 | A * | 11/1939 | Henne | ............................ 132/323 |
| 3,799,177 | A | 3/1974 | Bragg | |
| 4,304,246 | A | 12/1981 | Yafai | |
| 4,519,408 | A | 5/1985 | Charatan | |
| 4,655,233 | A | 4/1987 | Laughlin | |
| 4,941,488 | A | 7/1990 | Marxer et al. | |
| 4,982,752 | A | 1/1991 | Rodriguez | |
| 5,067,503 | A | 11/1991 | Stile | |
| 5,123,432 | A | 6/1992 | Wyss | |
| 5,127,415 | A | 7/1992 | Preciutti | |
| 5,222,510 | A | 6/1993 | Zuehlsdorf | |
| 5,224,501 | A | 7/1993 | McKenzie | |
| 5,435,330 | A * | 7/1995 | Dix | ................. 132/323 |
| 5,469,874 | A | 11/1995 | Meyer et al. | |
| 5,564,446 | A | 10/1996 | Wiltshire | |
| 5,860,435 | A | 1/1999 | Hippensteel | |
| 5,915,392 | A * | 6/1999 | Isaac | ............................. 132/200 |
| 6,019,109 | A | 2/2000 | Moore | |
| 6,065,480 | A | 5/2000 | Mader | |
| 6,161,556 | A | 12/2000 | Gutierrez | |
| 6,220,257 | B1 | 4/2001 | Meyer et al. | |
| 6,895,977 | B2 | 5/2005 | Guo | |
| 2004/0134510 | A1 | 7/2004 | van Vilsteren et al. | |
| 2010/0018547 | A1 * | 1/2010 | Roemuss | ....................... 132/323 |

FOREIGN PATENT DOCUMENTS

WO      WO8807354      10/1988

* cited by examiner

*Primary Examiner* — Nicholas Lucchesi
*Assistant Examiner* — Niyati D Shah
(74) *Attorney, Agent, or Firm* — Webb IP Law Group; Jason P. Webb; Danny Y. H. Cheng

(57) ABSTRACT

A flossing device including a first elongated member and a second elongated member each including a channel disposed at a top end, wherein each channel includes a first cross-sectional spacing and a second cross-sectional spacing, wherein the second cross-sectional spacing is less than the first cross-sectional spacing, and the second cross-sectional spacing is closer to a top edge of the first elongated member than the first cross-sectional spacing. The flossing device includes a floss string having a first end including an enlarged portion disposed within the channel of the elongated members, and sized to be substantially larger than the second cross-sectional spacing. The floss string may include a second end coupled to a top end of the second elongated member. The flossing device includes a seal and an aperture disposed on a surface of the elongated members and are disposed adjacent the channel.

11 Claims, 6 Drawing Sheets

FLOSSING DEVICE

BACKGROUND OF THE INVENTION

1. Field of the Invention

The present invention relates to dental tools, specifically flossing devices.

2. Description of the Related Art

Dental floss is generally a bundle of thin nylon filaments or a plastic (Teflon or polyethylene) ribbon used to remove food and dental plaque from teeth. The floss is gently inserted between the teeth and scraped along the teeth sides, especially close to the gums. Dental floss may be flavored or unflavored, and waxed or unwaxed. An alternative tool to achieve a similar effect is the interdental brush.

Dental floss is commonly supplied in plastic dispensers that contain 10 to 50 meters of floss. After pulling out the desired amount, the floss is pulled against a small protected blade in the dispenser to sever it. Dental floss is held between the fingers. The floss is guided between each tooth and under the gumline to remove particles of food stuck between teeth and dento-bacterial plaque that adhere to such dental surfaces. Ideally using a C-shape, the floss is curved around a tooth and placed under the gumline, and then moved away from the gumline, the floss scrapes the side of each tooth, and can also clean the front or back of the tooth. Gently moving the floss from below the gumline to away from the gumline removes dento-bacterial plaque attached to teeth surfaces above and below the gumline. A clean section of floss can be used to clean each tooth to avoid transmitting plaque bacteria from one tooth to another.

There are many different kinds of dental floss commonly available. The most important variable is thickness. If the floss is too thick for the space between a pair of teeth then it will be difficult or impossible to get the floss down between the teeth. On the other hand, if the floss is too thin, it may be too weak and break. Different floss will suit different mouths, and even different parts of one mouth. This is because some teeth have a smaller gap between them than others. It's possible that thicker floss does a better job of scraping bacterial plaque off teeth, given that there is space enough between the teeth to use it. When a piece of hard food is tightly wedged between the teeth, one may need to switch to thinner floss, because thick floss cannot get past the food. It is possible to split some kinds of dental floss lengthwise generating a pair of thinner pieces that are much weaker but sometimes usable. This is possible because some kinds of dental floss are made of many very thin strands that are not woven together but rather run more or less in parallel. This can also be useful if the dental floss you have is too thick for you, for any other reason, and you do not have access to any other, for example when travelling in a foreign country.

Specialized plastic wands, or floss picks, have been produced to hold the floss. These may be attached to or separate from a floss dispenser. While wands do not pinch fingers like regular floss can, using a wand may be awkward and can also make it difficult to floss at all the angles possible with regular floss. These types of flossers also run the risk of missing the area under the gum line that needs to be flossed. On the other hand, the enhanced reach of a wand can make flossing the back teeth easier.

Ergonomic flossers with improved handle for better grip and swiveling floss heads allow easy access to any pair of teeth in the mouth, to the front teeth as well as to the rear teeth. Their floss heads also feature a lateral flexibility that enables improved control for the dental floss to hug the sides of the teeth and clean under the gum line without the danger of hurting the gums. Occasional flossing and/or improper flossing can typically lead to bleeding gums. The main cause of the bleeding is inflammation of the gingival tissue due to gingivitis.

Some improvements have been made in the field. Examples of references related to the present invention are described below in their own words, and the supporting teachings of each reference are incorporated by reference herein:

U.S. Pat. No. 6,895,977, issued to Guo, discloses a dental flossing tool for dispensing floss for cleaning the user's teeth. A handle body surrounds a cavity and has a lead riser from which dental floss is dispensed for use. The floss is wound upon a spool that rotates inside the cavity. Floss is paid out from the spool and emerges from a hole in the tip of the lead riser. A button or handle is slidably mounted upon the apparatus for controlling the longitudinal movement of a retainer within the cavity of the apparatus. By sliding the button handle forward and backward, the user can disengage and engage the retainer with a baffle attached to the spool inside the body of the apparatus. When the retainer is in contact with the baffle, the spool is prevented from rotating, thereby stopping any further floss from being dispensed. When the retainer is disengaged out of contact with the baffle, the spool is free to rotate to pay out floss. A removable protector is provided for covering the lead riser and a floss cutter blade attached to the exterior of the apparatus. The protector can be removed to the back end of the apparatus to extend its graspable portion for easier handling.

U.S. Pat. No. 6,019,109, issued to Moore, discloses a dental flossing tool and method for flossing of the teeth using that tool is provided. The tool includes two elongated, rod-shaped handle elements and a length of dental floss that is removably secured at its opposite ends to respective ones of the handle elements at their terminal ends. Each handle element is provided with a bulb at the terminal end to which the floss is attached with the bulbs being larger in transverse cross-section relative to the longitudinal axis of its handle element than is the adjacent portion of the handle element. This results in a depressed annular region in which floss is wound and functions to retain the floss on a handle element. Each handle element includes a hand-grip section disposed in remote relationship to the terminal end provided with a bulb enabling a user to grip the element in a respective hand for support thereof and independent manipulation in effecting a flossing operation. The user holds the handle elements in separated relationship to maintain the floss extending between the terminal ends taut as an operative flossing section while inserting it between a pair of adjacent teeth and moving it to effect removal of debris. At intermittent intervals the user revolves the handle elements to concurrently unreel a length of floss from one and reel a length onto the other thereby placing an unused section of floss in an operative position and placing the previously used section on a handle element for storage until being discarded upon termination of a flossing operation.

U.S. Pat. No. 5,915,392, issued to Isaac, discloses a toothpick apparatus of the present invention consists of an elongated cylindrical device 13 having a thicker middle portion 17 tapering away from the middle toward opposing ends or points 19. The toothpick has a perforated area or break point near its middle 17 whereby when the toothpick is broken a useable length of dental floss 23 is exposed. The dental floss 23 is contained within layers of thin wood 21 which are rolled in order to form the toothpick. Additional embodiments of the present invention are also described.

U.S. Pat. No. 5,224,501, issued to McKenzie, discloses an improved device for holding and manipulating dental floss for the removal of food particles, tartar and plaque from the teeth is described in which a loop of dental floss is connected between a pair of separate handles; the loop of dental floss being long enough to permit lateral motion across the tooth surface. The devices are either disposable or sterilizable for reuse.

U.S. Pat. No. 5,123,432, issued to Wyss, discloses a double-ended hand held flossing tool with stressing means is provided which uses a loop of floss made integral with the frame members of the tool, and provides stressing action through fingertip manipulation of the members. The loop is integral and structural to the tool, thus my tool design gains the advantage of stability by virtue of two members being integral with a floss loop molded directly into the construction of the frame members of the tool.

The inventions heretofore known suffer from a number of disadvantages which include being limited in application, being limited in use, being difficult to use, being difficult to re-use, being expensive, being difficult to manufacture, failing to adequately clean between teeth, damaging gums, not clearly communicating to a user when a device has already been used, requiring significant manual dexterity to operate, and the like.

What is needed is a flossing device that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available flossing devices. Accordingly, the present invention has been developed to provide a flossing device that may be quickly and easily be ready for use.

According to one embodiment of the invention, there is a flossing device that may include a pair of sticks (elongated members) coupled by a length of floss, wherein the length of floss may be selectably extendable. There may be a first elongated member. The first elongated member may include a channel that may be disposed at a top end of the first elongate member. The channel may include a first cross-sectional spacing and a second cross-sectional spacing. The second cross-sectional spacing may be less than the first cross-sectional spacing and the second cross-sectional spacing may be closer to a top edge of the first elongated member than the first cross-sectional spacing.

The flossing device may also include a second elongated member. The second elongated member may include a channel that may be disposed at a top end of the second elongated member. The channel may include a first cross-sectional spacing and a second cross-sectional spacing. The second cross-sectional spacing may be less than the first cross-sectional spacing, and the second cross-sectional spacing may be closer to a top edge of the second elongated member than the first cross-sectional spacing.

The flossing device may include a floss string. The floss string may include a first end. The first end may include an enlarged portion that may be disposed within the channel of the first elongated member. The first end may be sized to be substantially larger than the second cross-sectional spacing. The floss string may include a second end that may be coupled to a top end of the second elongated member. The floss string may be knotted at both ends, thereby forming the enlarged portions.

The channel of the flossing device may include a first chamber and a second chamber. The first chamber and the second chamber may be in communication with one another. The first chamber may be disposed substantially above the second chamber. The second chamber may include a larger interior volume than the first chamber.

The channel of the flossing device may include a stepped chamber. The stepped chamber may includes a base region, a middle region, and/or a top region. The base region may be larger than the middle region, and/or the middle region may be larger than the top region. The top region may be disposed on top of the middle region and/or the middle region may be disposed on the base.

The channel of the flossing device may include a frustoconical chamber. The frustoconical chamber may include a first end and a second end, the second end may include a base that may be tapering towards a peak of the first end.

The flossing device may include a first mode and a second mode. The first mode may include a first elongated member coupled to a second elongated member along a top region/surface of the elongated members. The second mode may include the first elongated member and the second elongated member not being coupled along the top region/surface.

The flossing device may include a seal and a aperture that may be disposed on a surface of the first elongated member and the second elongated member. The seal and the aperture may be disposed adjacent the channel of the first elongated member and the second elongated member.

According to one embodiment of the invention, there is a method of flossing using a flossing device. The method may include the step of grasping a pair of elongated members coupled together along an end. The method may include pulling the elongated members apart until the coupling therebetween breaks. The method may also include pulling the elongated members apart until a floss string therebetween retracts to a usable length. The method may include inserting the floss string in between teeth. The method may include the step of pulling the pair of elongated members until a knot of the floss string is wedged within a channel of an elongated member. The method may include pulling the pair of elongated members until a pair of knots of the floss string is wedged within a channel of the pair of elongated members. The method may include removing and replacing a seal of the pair of elongated members. The method may further include the step of manipulating the pair of elongated members in between teeth, from a side base of a tooth to the top side of a tooth and therebetween.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawing(s). It is noted that the drawings of the invention are not to scale. The drawings are mere schematics representations, not intended to portray specific parameters of the invention. Understanding that these drawing(s) depict only typical embodiments of the invention and are not, therefore, to be considered to be limiting its scope, the invention will be described and explained with additional specificity and detail through the use of the accompanying drawing(s), in which.

DETAILED DESCRIPTION OF THE INVENTION

Figure 1:
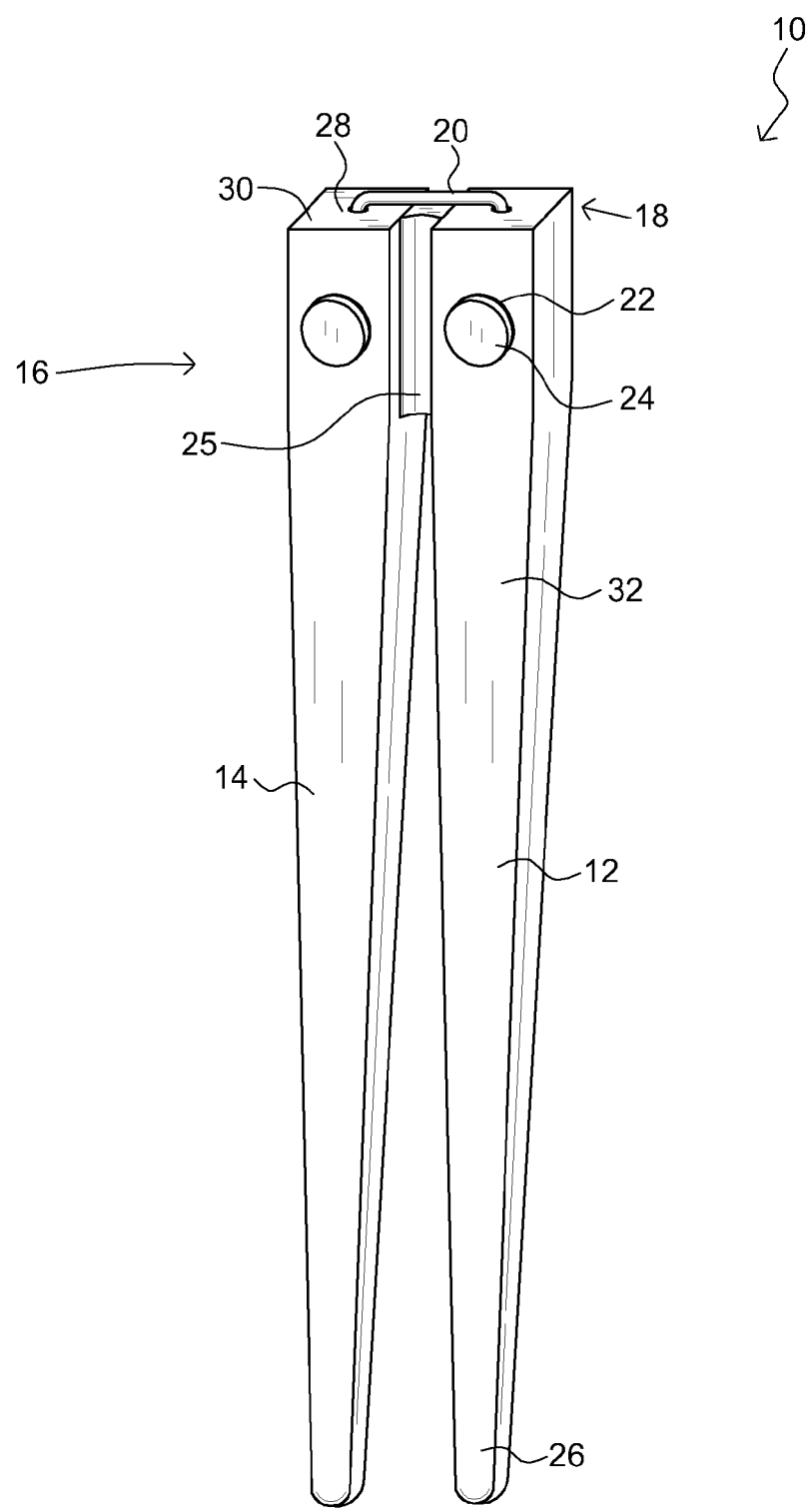
FIG. 1 is a perspective view of a flossing device in a first mode, according to one embodiment of the invention.

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," an "example," and similar language throughout this specification may, but do not necessarily, all refer to the same embodiment, to different embodiments, or to one or more of the figures. Additionally, reference to the wording "embodiment," "example" or the like, for two or more features, elements, etc. does not mean that the features are necessarily related, dissimilar, the same, etc.

Each statement of an embodiment, or example, is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions, and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps. "Comprising" is to be interpreted as including the more restrictive terms "consisting of" and "consisting essentially of."

FIG. 1 is a perspective view of a flossing device in a first mode, according to one embodiment of the invention. There is shown a first elongated member 12 and a second elongated member 14 of a flossing device 10 in a first mode 16, wherein the first and second elongated members are coupled one to the other by a connector 25 and by a floss string 20. The illustrated flossing device 10 is similar to a pair of disposable chopsticks wherein the top ends are coupled by extendable floss.

The flossing device 10 includes a first elongated member 12 and a second elongated member 14. The illustrated flossing device 10 is in a first mode 16, wherein the first elongated member 12 and the second elongated member 14 are coupled along a top end 18 by a connector 25 and an extendable floss string 20. The illustrated connector is a connecting strip of material that is shaped, sized or otherwise configured to break/separate/disengage/etc. when subject to an appropriate force in a manner that maintains the integrity of the elongated members while permitting the elongated members to be distanced one from the other. In one embodiment, a connector is a narrow neck such as commonly used with disposable wooden chopsticks. In one embodiment, a connector is an adhesive layer, a brittle material, paired snaps, hook and loop connectors, and/or other connectors.

The illustrated first elongated member 12 and the second elongated member 14, when in the first mode 16, are positioned parallel to each other. The illustrated first elongated member 12 and the illustrated second elongated member 14 each include a tapered end 26, opposite of the top end 18, configured to provide gripping handles to a user. The illustrated elongated members 12 and 14 are substantially rigid members formed of a material suitable for placement in the mouth of a user and suitable for grasping in the hands of a user. While varieties of wood and plastic are expected to be suitable materials, it is understood that other materials may also be suitable, including but not limited to composite materials. Elongated members (sticks, handles, grips, manipulators, arms, etc.) may include features and/or structures that may facilitate use, such as but not limited to rounded top ends, gripping ridges, curved or angled portions, and the like and combinations thereof.

The illustrated flossing device 10 includes a floss string 20 disposed within each of the first elongated member 12 and the second elongated member 14 and extends out a top aperture 28 disposed on a top surface 30 of each of the elongated members 12, 14. It is understood that floss string may extend out of a top end through a surface other than a top surface of the top end. Floss string may include filaments, ribbons, woven fibers, and the like or combinations thereof. It may be augmented by wax, flavorings, coatings, and the like and combinations thereof.

The illustrated flossing device 10 includes a seal 24 and an aperture 22 disposed on a side surface 32 of the first elongated member 12 and of the second elongated member 14. The seal 24 and the aperture 22 are disposed adjacent a channel, disposed within each of the first elongated member 12 and of the second elongated member 14. The aperture 22 is in communication with the channel, thereby facilitating manufacture of the flossing device by providing access to a bottom portion of the channel. The seal 24 and the aperture 22 are configured to provide access to the channel of each of the first elongated member 12 and the second elongated member 14. The seal 24 is configured to seal the aperture 22 and secure the contents of the channel therein. In one non-limiting example, the seal is a hardened polymer that has been disposed within the aperture in a fluid form and then caused to be hardened therein. In another non-limiting example, the seal includes an elastic material shaped and sized to friction-fit within the aperture. In another non-limiting example, the seal snaps into place. In another non-limiting example, the seal is threaded to match threads of the aperture and screws into the aperture. The floss string 20 is contained within the channel of each of the first elongated member 12 and the second elongated member 14.

Figure 2:
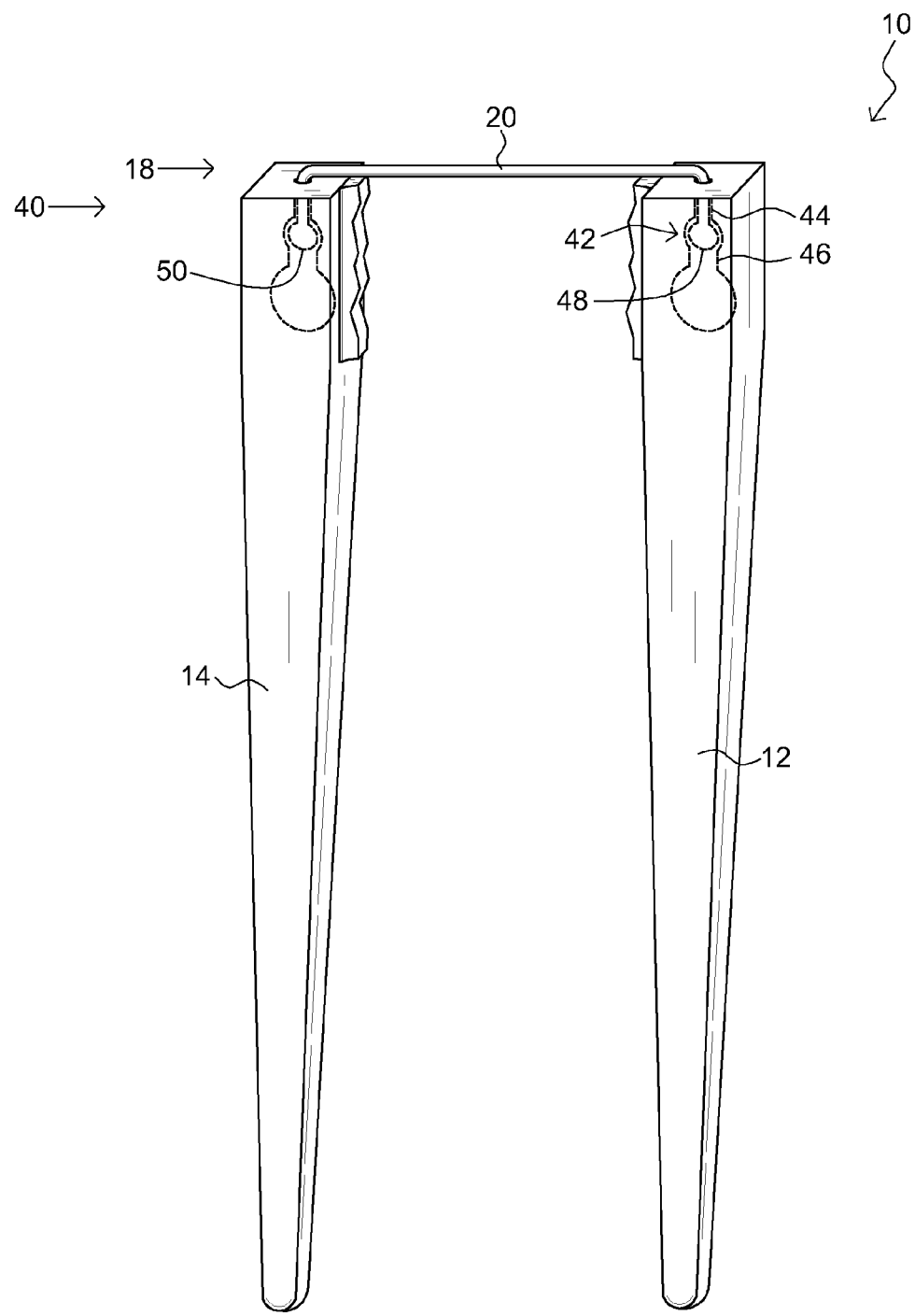
FIG. 2 is a perspective view of a flossing device in a second mode, according to one embodiment of the invention.

FIG. 2 is a flossing device in a second mode, according to one embodiment of the invention. There is shown a first elongated member 12 and a second elongated member 14 of a flossing device 10 in a second mode 40, wherein the elongated members are not connected by a connector and still connected by an extended floss string such that the floss string may be disposed between adjacent teeth of a user by manipulating the elongated members.

The illustrated flossing device 10 includes a first elongated member 12 and a second elongated member 14 in a second mode 40. The illustrated second mode 40 includes the first elongated member 12 and the second elongated member 14 being uncoupled along a top end 18 of the members 12, 14. The first elongated member 12 and the second elongated member 14 each include a channel 42 disposed about the top end 18 of the first elongated member 12 and the second elongated member 14. The channel 42 includes a first cross-sectional spacing 46 and a second cross-sectional spacing 44. Cross-sectional spacing is that spacing that the end of the floss string experiences as it rest in the channel. A cross-sectional spacing substantially smaller than the end of the floss string will not permit the floss string to pass therethrough. A cross-sectional spacing that is substantially similar to the end of the floss string will permit the floss string to pass thereby when force is applied. A cross-sectional spacing substantially larger than the end of the floss string will permit the end of the floss string to move freely about the associate region. The second cross-sectional spacing 44 is less than the first cross-sectional spacing 46, and the second cross-sectional spacing 44 is disposed closer to the top end 18, of the first elongated member 12 and the second elongated member 14, than the first cross-sectional spacing 46. Wherein the second cross-sectional spacing 44 is smaller than what will allow the string to be pulled completely out of the channel, the string may be extended an amount when the sticks are pulled apart while still permitting the floss string to be taut while in use. The illustrated channel includes a pair of bulbous chambers wherein the end of the floss string may rest.

The flossing device 10 includes a floss string 20. The floss string 20 includes a first end 48 having an enlarged portion that is disposed within the channel 42 of the first elongated member 12. The first end 48 is sized to be substantially larger than the second cross-sectional spacing 44. The floss string 20 includes a second end 50 having an enlarged portion that is disposed within the channel 42 of the second elongated member 14. The second end 50 is sized to be substantially larger than the second cross-sectional spacing 44 of the second elongated member 14. The illustrated floss string 20 is knotted at both ends 48, 50.

In operation of one embodiment of the invention, a user grasps a pair of elongated members of a flossing device at a tapered end. The user pulls the elongated members apart, thereby separating the elongated members at a top end and tightening a floss string between the elongated members. The user inserts the floss string in between teeth. The user manipulates each elongated member to position the floss string in between teeth to floss there between.

Figure 3:
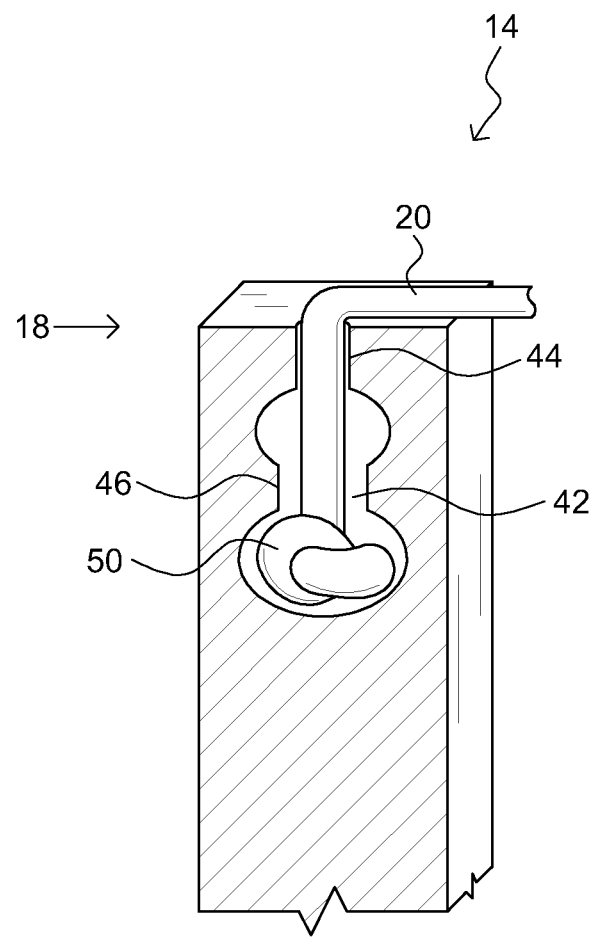
FIG. 3 is a partial cross-sectional view of a first elongated member of a flossing device, according to one embodiment of the invention.

FIG. 3 is a partial cross-sectional view of a first elongated member of a flossing device, according to one embodiment of the invention. There is shown a second elongated member 14 of a flossing device.

The flossing device includes a second elongated member 14. The illustrated second elongated member 14 includes a channel 42 that is disposed at a top end 18 of the second elongated member 14. The channel 42 includes a first cross-sectional spacing 46 and a second cross-sectional spacing 44. The second cross-sectional spacing 44 is less than the first cross-sectional spacing 46, and the second cross-sectional spacing 44 is closer to the top edge 18 of the second elongated member 14, than the first cross-sectional spacing 46.

The flossing device includes a floss string 20. The illustrated floss string 20 includes a second end 50 having an enlarged portion that is disposed within the channel 42 of the second elongated member 14. The second end 50 is sized to be substantially larger than the second cross-sectional spacing 44 of the second elongated member 14. The illustrated second end 50 of the floss string 20 is knotted. The second end 50 rests in the first cross-sectional spacing 46 in a first mode. The second end 50 in a second mode is retracted into the channel 42 and secures or wedges into the second cross-sectional spacing 44, thereby tightening the floss string 20 between the pair of elongated members.

The illustrated channel 42 of the flossing device includes a first chamber 44 and a second chamber 46. The first chamber 44 and the second chamber 46 are in communication with one another. The illustrated first chamber 44 is disposed substantially above the second chamber 46. The second chamber 46 includes a larger cross-sectional spacing then the first chamber 44.

Figure 4:
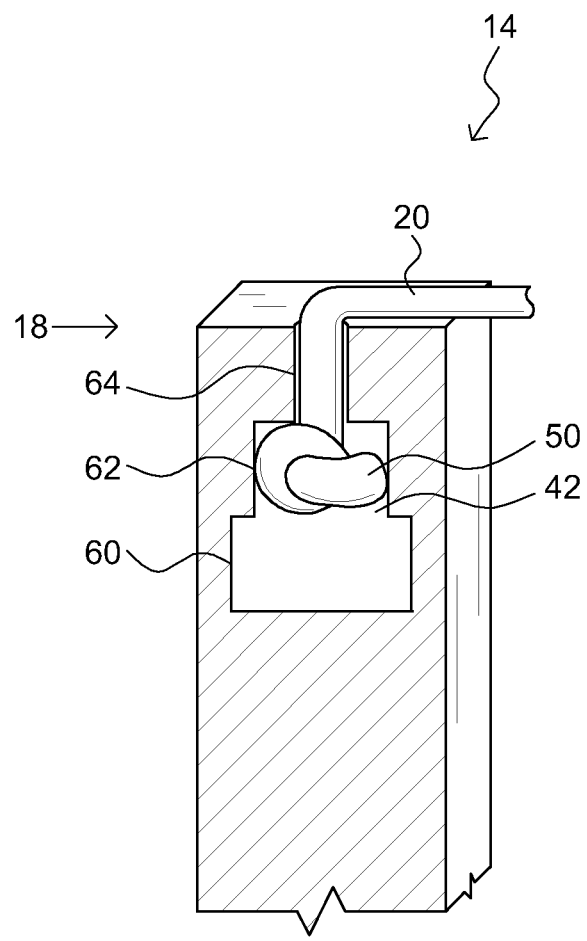
FIG. 4 is a partial cross-sectional view of a first elongated member of a flossing device, according to one embodiment of the invention.

FIG. 4 is a partial cross-sectional view of a first elongated member of a flossing device, according to one embodiment of the invention. There is shown a second elongated member 14 of a flossing device.

The flossing device includes a second elongated member. The illustrated second elongated member 14 includes a channel 42 that is disposed at a top end 18 of the second elongated member 14. The channel 42 includes a first cross-sectional spacing 60, a second cross-sectional spacing 62, and a third cross-sectional spacing 64. The third cross-sectional spacing 64 is less than the second cross-sectional spacing 62, and the second cross-sectional spacing is less than the first cross-sectional spacing 60. The third cross-sectional spacing 64 is closer to the top end 18 of the second elongated member 14 than the second cross-sectional spacing 62, and the second cross-sectional spacing 62 is closer to the top end 18 than the first cross-sectional spacing 60.

The flossing device includes a floss string 20. The illustrated floss string 20 includes a second end 50 having an enlarged portion that is disposed within the channel 42 of the second elongated member 14. The second end 50 is sized to be substantially larger than the third cross-sectional spacing 64. The second end 50 rests in the first cross-sectional spacing 60 in a first mode. The second end 50 in a second mode is retracted into the second cross-sectional spacing 62 and secures or wedges into the third cross-sectional spacing 64, thereby tightening the floss string 20 between the pair of elongated members.

The illustrated channel 42 of the flossing device includes a stepped chamber. The stepped chamber includes a base region 60, a middle region 62, and a top region 64. The base region 60 is substantially larger than the middle region 62, and the middle region 62 is larger than the top region 64. The top region 64 is disposed above the middle region 62 and the middle region 62 is disposed above the base region 60.

Figure 5:
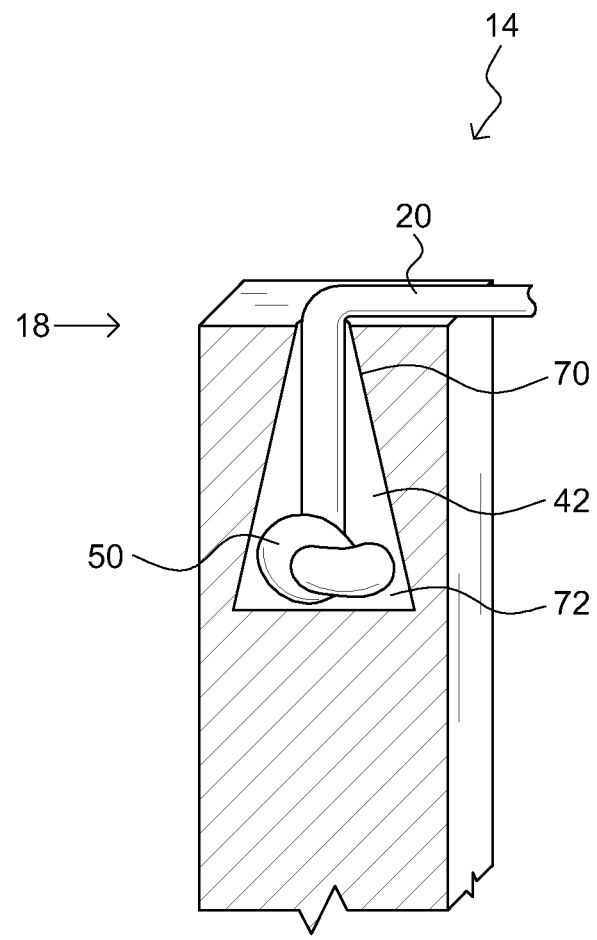
FIG. 5 is a partial cross-sectional view of a first elongated member of a flossing device, according to one embodiment of the invention.

FIG. 5 is a partial cross-sectional view of a first elongated member of a flossing device, according to one embodiment of the invention. There is shown a second elongated member 14 of a flossing device.

The flossing device includes a second elongated member 14. The second elongated member 14 includes a channel 42 disposed at a top end 18 of the second elongated member 14. The illustrated channel 42 includes a first cross-sectional spacing end 72 and a second cross-sectional spacing end 70. The second cross-sectional spacing end 70 is less than the first cross-sectional spacing end 72, and the second cross-sectional spacing end 70 is closer to the top end 18 of the second elongated member 14, than the first cross-sectional spacing end 72.

The flossing device includes a floss string 20. The floss string 20 includes second end 50 having an enlarged portion that is disposed within the channel 42 of the second elongated member 14. The second end 50 is sized to be substantially larger than the second cross-sectional spacing end 70. The second end 50 rests in the first cross-sectional spacing end 72 in a first mode. The second end 50 in a second mode is retracted into the channel 42 and secures or wedges into the second cross-sectional spacing 70, thereby tightening the floss string 20 between the pair of elongated members.

The illustrated channel 42 of the flossing device includes a frustoconical chamber. The frustoconical chamber includes a first end 70 and a second end 72, the second end 72 is includes a base that is configured to taper towards a peak of a first end 70.

Figure 6:
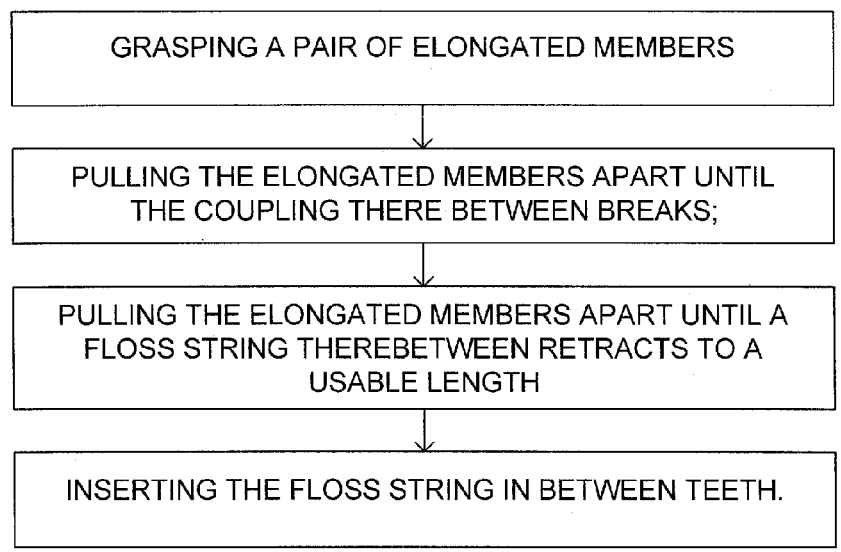
FIG. 6 is a flowchart of a method of flossing using a flossing device, according to one embodiment of the invention.

The present application presents a method of flossing using a flossing device (See FIG. 6), comprising one or more of the steps of: grasping a pair of elongated members coupled together along an end; pulling the elongated members apart until the coupling therebetween breaks; pulling the elongated members apart until a floss string therebetween retracts to a usable length; and/or inserting the floss string in between teeth. Such a method may also include pulling the pair of elongated members until a knot of the floss string is wedged within a channel of an elongated member; pulling the pair of elongated members until a pair of knots of the floss string is wedged within a channel of the pair of elongated members; removing and replacing a seal of the pair of elongated members; and/or manipulating the pair of elongated members in between teeth, from a side base of a tooth to the top side of a tooth and therebetween.

Floss string may be retracted using one or more of the following structures/systems: spools, springs or other bias members, fixed attachment with extra floss length stored in a chamber (such as by coiling), floss string having a portion thereof being sufficiently elastic and/or of sufficient length to provide usable retraction, Statements of Invention 1. A flossing device for flossing teeth, comprising
  i) a first elongated member comprising a channel disposed at a top end of the first elongate member, wherein the channel comprises a first cross-sectional spacing and a second cross-sectional spacing, wherein the second cross-sectional spacing is less than the first cross-sectional spacing and the second cross-sectional spacing is closer to a top edge of the first elongated member than the first cross-sectional spacing
  ii) a second elongated member, and
  iii) a floss string comprising;
    a) a first end which comprises an enlarged portion disposed within the channel of the first elongated member, and sized to be substantially larger than the second cross-sectional spacing, and
    b) a second end coupled to a top end of the second elongated member.

2. The device of the preceding statement, wherein the channel comprises a first chamber and a second chamber, wherein the first chamber and the second chamber are in communication; wherein the first chamber is disposed substantially above the second chamber; wherein the second chamber comprises a larger interior volume than the first chamber.

3. The device of any preceding statement, wherein the channel comprises a stepped chamber; wherein the stepped chamber comprises a base, a middle region, and a top region; wherein the base is larger than the middle region, and wherein the middle region is larger than the top region; wherein the top region is disposed on top of the middle region and the middle region is disposed on the base.

4. The device of any preceding statement, wherein the channel comprises a frustoconical chamber; wherein the frustoconical chamber comprises a first end and a second end; wherein the second end comprises a base tapering towards a peak of the first end.

5. The device of any preceding statement, wherein the device may occupy a first configuration or a second configuration; wherein in the first configuration the first elongated member is coupled to the second elongated member along a top region; and in the second configuration the first elongated member and the second elongated member are not coupled along a top region.

6. The device of any preceding statement, wherein the second elongated member comprises a channel disposed at a top end of the second elongated member, wherein the channel comprises a first cross-sectional spacing and a second cross-sectional spacing, wherein the second cross-sectional spacing is less than the first cross-sectional spacing and the second cross-sectional spacing is closer to a top edge of the second elongated member than the first cross-sectional spacing.

7. The device of any preceding statement, further comprising a seal and a aperture disposed on a surface of the first elongated member; wherein the seal and the aperture are disposed adjacent the channel of the first elongated member.

8. The device of statement 7, when dependent upon statement 6, further comprising a seal and an aperture disposed on a surface of the second elongated member; wherein the seal and the aperture are disposed adjacent to the channel of the second elongated member.

9. The device of any preceding statement, wherein the floss string is knotted at both ends.

10. A method of flossing teeth using a flossing device, comprising the step of grasping a pair of elongated members coupled together along an end.

11. The method of statement 10, comprising pulling the elongated members apart until the coupling therebetween breaks, and optionally further comprising pulling the elongated members apart until a floss string therebetween retracts to a usable length.

12. The method of statement 11, comprising inserting the floss string in between teeth and optionally further comprising manipulating the floss string in between teeth, from a side base of a tooth to the top side of a tooth and therebetween.

13. The method of statement 12, comprising pulling the pair of elongated members until a knot of the floss string is wedged within a channel of an elongated member.

14. The method of statement 13, comprising pulling the pair of elongated members until a pair of knots of the floss string is wedged within a channel of the pair of elongated members.

15. The method of statement 14, comprising removing and replacing a seal of the pair of elongated members.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

For example, although the Figures illustrate a pair of elongated members having a square top surface tapering down towards a point, one skilled in the art would appreciate that the first elongated member and the second elongated member may vary in: size, shape, design, configuration, color, length, height, width, curvature, arch, etc., and still perform its intended function.

While the figures illustrate a chopstick-style configuration, it is envisioned that the size of the flossing device may be substantially different than a typical pair of chopsticks. As a non-limiting example, a flossing device may be substantially smaller than a pair of chopsticks, such as but not limited to being sized similarly to other flossing aids.

Additionally, although the figures illustrate a particular retraction mechanism for the floss string, it is envisioned that such mechanisms are plethoric.

It is envisioned that elongated members may be shaped other than straight to facilitate reach, manipulation, and/or handling of the floss.

It is expected that there could be numerous variations of the design of this invention. An example is that the portions described herein may include decorative elements, including but not limited to three-dimensional representations of animals, people, licensed characters and the like.

Finally, it is envisioned that the components of the device may be constructed of a variety of materials, such as but not limited to: plastics, plastic composites, rubber, rubber composites, metals, metal alloys, glass, textiles, etc. and still perform its intended function.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:

1. A flossing device, comprising:
   a) a first elongated member including a channel disposed at a top end of the first elongate member, wherein the channel includes a first cross-sectional spacing and a second cross-sectional spacing, wherein the second cross-sectional spacing is less than the first cross-sectional spacing, and the second cross-sectional spacing is closer to a top edge of the first elongated member than the first cross-sectional spacing; wherein the channel includes a stepped chamber; wherein the stepped chamber includes a base, a middle region, and a top region; wherein the base is larger than the middle region, and wherein the middle region is larger than the top region; wherein the top region is disposed on top of the middle region and the middle region is disposed on the base, thereby the top region forms the second-cross-sectional spacing of the channel and the middle region forms the first cross-sectional spacing of the channel;
   b) a second elongated member, coupled to the first elongated member by a breakaway coupling; and
   c) a floss string, including:
      c1) a first end including an enlarged portion disposed within the channel of the first elongated member, and sized to be substantially larger than the second cross-sectional spacing; and
      c2) a second end coupled to a top end of the second elongated member.

2. The device of claim 1, wherein the device further includes a first mode and a second mode; wherein the first mode includes the first elongated member coupled to the second elongated member along the top end; wherein the second mode includes the first elongated member and the second elongated member are not coupled along the top end.

3. The device of claim 1, wherein the second elongated member includes a channel disposed at a top end of the second elongated member, wherein the channel includes a first cross-sectional spacing and a second cross-sectional spacing, wherein the second cross-sectional spacing is less than the first cross-sectional spacing, and the second cross-sectional spacing is closer to a top edge of the second elongated member than the first cross-sectional spacing.

4. The device of claim 1, wherein the device further includes a seal and a aperture disposed on a surface of the first elongated member and the second elongated member; wherein the seal and the aperture are disposed adjacent the channel of the first elongated member and the second elongated member.

5. The device of claim 1, wherein the floss string is knotted at both ends.

6. A method of flossing using a flossing device, comprising the steps of:
   a) grasping a pair of elongated members coupled together along an end; wherein a first elongated member of the pair of elongated members includes a channel disposed at a top end of the first elongate member, wherein the channel includes a first cross-sectional spacing and a second cross-sectional spacing, wherein the second cross-sectional spacing is less than the first cross-sectional spacing, and the second cross-sectional spacing is closer to a top edge of the first elongated member than the first cross-sectional spacing; wherein the channel includes a stepped chamber; wherein the stepped chamber includes a base, a middle region, and a top region; wherein the base is larger than the middle region, and wherein the middle region is larger than the top region; wherein the top region is disposed on top of the middle region and the middle region is disposed on the base, thereby the top region forms the second-cross-sectional spacing of the channel and the middle region forms the first cross-sectional spacing of the channel;
   b) pulling the elongated members apart until the coupling therebetween breaks;
   c) pulling the elongated members apart until a floss string therebetween retracts to a usable length and an enlarged portion of the floss becomes wedged, being in an initial un-wedged state, within a region of an elongated member; and d) inserting the floss string in between teeth.

7. The method of claim 6, further comprising the step of pulling the pair of elongated members until a knot of the floss string is wedged within a channel of an elongated member.

8. The method of claim 7, further comprising the step of pulling the pair of elongated members until a pair of knots of the floss string is wedged within a channel of the pair of elongated members.

9. The method of claim 8, further comprising the step of removing and replacing a seal of the pair of elongated members.

10. The method of claim 9, further comprising the step of manipulating the pair of elongated members in between teeth, from a side base of a tooth to the top side of a tooth and therebetween.

11. A flossing device, comprising a pair of elongated members coupled by a breakaway coupling and further coupled by a retractable length of floss having an enlarged portion sized to be wedged into a channel of an elongated member when the pair of elongated members are pulled apart and residing, un-wedged, in a chamber of the elongated member when the pair of elongated members are coupled by the breakaway coupling, and further comprising:

a) a first elongated member including a channel disposed at a top end of the first elongate member, wherein the channel includes a first cross-sectional spacing and a second cross-sectional spacing, wherein the second cross-sectional spacing is less than the first cross-sectional spacing, and the second cross-sectional spacing is closer to a top edge of the first elongated member than the first cross-sectional spacing;

b) a second elongated member; wherein the second elongated member includes a channel disposed at a top end of the second elongated member, wherein the channel includes a first cross-sectional spacing and a second cross-sectional spacing, wherein the second cross-sectional spacing is less than the first cross-sectional spacing, and the second cross-sectional spacing is closer to a top edge of the second elongated member than the first cross-sectional spacing;

c) a floss string, including:
c1) a first end including an enlarged portion disposed within the channel of the first elongated member, and sized to be substantially larger than the second cross-sectional spacing;
c2) a second end coupled to a top end of the second elongated member;
wherein the floss string is knotted at the first end and at the second end;

d) a first mode and a second mode; wherein the first mode includes the first elongated member coupled to the second elongated member along the top end; wherein the second mode includes the first elongated member and the second elongated member are not coupled along the top end; and e) a seal and a aperture disposed on a surface of the first elongated member and the second elongated member; wherein the seal and the aperture are disposed adjacent the channel of the first elongated member and the second elongated member; wherein the channel includes a stepped chamber; wherein the stepped chamber includes a base, a middle region, and a top region; wherein the base is larger than the middle region, and wherein the middle region is larger than the top region; wherein the top region is disposed on top of the middle region and the middle region is disposed on the base, thereby the top region forms the second-cross-sectional spacing of the channel and the middle region forms the first cross-sectional spacing of the channel.

\* \* \* \* \*